United States Patent
Arnal et al.

(10) Patent No.: US 8,701,670 B2
(45) Date of Patent: Apr. 22, 2014

(54) TRACKABLE OCCLUSION DEVICE AND CATHETER SYSTEM

(75) Inventors: Kevin R. Arnal, Excelsior, MN (US); James R. Mujwid, Crystal, MN (US)

(73) Assignee: Bayer Essure Inc., Milpitas, CA (US)

(*) Notice: Subject to any disclaimer, the term of this patent is extended or adjusted under 35 U.S.C. 154(b) by 729 days.

(21) Appl. No.: 12/769,534

(22) Filed: Apr. 28, 2010

(65) Prior Publication Data
US 2010/0275925 A1 Nov. 4, 2010

Related U.S. Application Data

(60) Provisional application No. 61/173,835, filed on Apr. 29, 2009.

(51) Int. Cl.
*A61F 6/06* (2006.01)

(52) U.S. Cl.
USPC .................... 128/831; 623/1.11; 623/1.15

(58) Field of Classification Search
USPC .............. 128/830–831; 623/1.23–1.24, 1.34, 623/1.36, 1.11, 1.12, 1.15; 606/108, 606/191–192, 194–195, 198
See application file for complete search history.

(56) References Cited

U.S. PATENT DOCUMENTS

| | | | |
|---|---|---|---|
| 5,743,905 A * | 4/1998 | Eder et al. | 606/32 |
| 5,792,154 A * | 8/1998 | Doan et al. | 606/151 |
| 6,296,622 B1 * | 10/2001 | Kurz et al. | 604/93.01 |
| 6,503,271 B2 * | 1/2003 | Duerig et al. | 623/1.15 |
| 6,705,323 B1 | 3/2004 | Nikolchev et al. | |
| 6,763,833 B1 | 7/2004 | Khera et al. | |
| 7,070,613 B2 * | 7/2006 | Weber et al. | 623/1.11 |
| 7,179,291 B2 * | 2/2007 | Rourke et al. | 623/2.36 |
| 7,243,408 B2 * | 7/2007 | Vietmeier | 29/447 |
| 7,326,245 B2 * | 2/2008 | Rosenthal et al. | 623/1.42 |
| 8,181,653 B2 * | 5/2012 | Tal et al. | 128/831 |
| 2005/0192616 A1 | 9/2005 | Callister et al. | |
| 2005/0209633 A1 | 9/2005 | Callister et al. | |
| 2008/0021544 A1 * | 1/2008 | Majercak et al. | 623/1.36 |
| 2009/0178682 A1 * | 7/2009 | Tal et al. | 128/831 |

\* cited by examiner

*Primary Examiner* — Tatyana Zalukaeva
*Assistant Examiner* — Camtu Nguyen
(74) *Attorney, Agent, or Firm* — Blakely, Sokoloff, Taylor & Zafman LLP

(57) ABSTRACT

An occlusion device and catheter delivery system are disclosed. The occlusion device may include an expandable member, an extended arm directly connected to the expandable member and extending distally therefrom, and a distal ball tip on a distal end of the extended arm. The extended arm and distal ball tip can function to steer the catheter delivery system when tracking through a body lumen to reach the target delivery site.

14 Claims, 3 Drawing Sheets

TRACKABLE OCCLUSION DEVICE AND CATHETER SYSTEM

RELATED APPLICATIONS

The present application claims priority to U.S. Provisional Application Ser. No. 61/173,835 filed Apr. 29, 2009, which is incorporated herein by reference.

BACKGROUND

This invention generally relates to the field of occlusion devices, delivery systems for such devices and the method of using such devices and systems in the occlusion of body passageways. The invention is particularly useful for occluding reproductive lumens such as a female patient's fallopian tubes or a male patient's vas deferens to provide contraception.

Conventional contraceptive strategies generally fall within three categories: physical barriers, drugs and surgery. While each have certain advantages, they also suffer from various drawbacks. Barriers such as condoms and diaphragms are subject to failure due to breakage, displacement and misplacement. Drug strategies, such as the pill and Norplant™, which rely on artificially controlling hormone levels, suffer from known and unknown side-effects from prolonged use. Surgical procedures, such as tubal ligation and vasectomy, are very effective, but involve the costs and attendant risks of surgery, and are frequently not reversible.

Recently, minimally invasive treatments have be proposed which deploy occluding stent-like devices within reproductive lumens, e.g. the fallopian tubes or vas deferens, as a contraceptive alternative to tubal ligation or vasectomy. In application, the occluding stent-like devices are advanced to the target site of the body lumen utilizing a catheter system. Care must be taken so as to not kink the catheter system during advancement, as well as to avoid perforating the reproductive lumen with the catheter system.

SUMMARY

The present invention relates to occlusion devices and methods for advancing a catheter delivery system through a body lumen, particularly a reproductive body lumen such as a female patient's fallopian tube or a male patient's vas deferens.

Occlusion devices in accordance with embodiments of the invention are configured for deployment within the patient's body lumen such as a reproductive lumen. The occlusion device may include an expandable member, an extended arm directly connected to the expandable member and extending distally therefrom, and a distal ball tip on a distal end of the extended arm. A catheter delivery system in accordance with embodiments of the invention may include a delivery catheter and an occlusion device at least partially placed within the delivery catheter, where the distal ball tip and at least a portion of the extended arm are outside of the delivery catheter, and the expandable member is inside the catheter. As such the extended arm and distal ball tip can function to steer the catheter delivery system when tracking through a body lumen to reach the target delivery site. The catheter delivery system may be defined by a tapered beam flexibility profile to deter kinking of the catheter system during advancement. In addition to the flexibility profile, the distal ball tip may help avoid perforating the reproductive lumen with the catheter system during tracking. While embodiments of the invention are described with reference to a single extended arm and distal ball tip, the catheter delivery system and occlusion device may also include a plurality of extended arms, at least a portion of which are outside of the delivery catheter, with a distal ball tip on a distal end of each of the plurality of extended arms. In addition, while the distal ball tip is characterized as a ball which may have a diameter, it is not necessary that the distal ball tip be spherical or be characterized as having a diameter.

The expandable member can be self-expandable from a first configuration within the delivery catheter to a second larger configuration when deployed, or expanded by other means such as an inflatable balloon placed within and removable from the expandable member. In an embodiment, the expandable member is a stent-like frame. For example, the stent-like frame can be formed of a stainless steel, nickel-titanium (NiTi) alloy (shape memory and superelastic), NiCoCrMo alloy (also known as MP35N, a trademark of SPS Technologies, Inc.), CoCrNi alloy (also known as ELGILOY, a trademark of Elgiloy Corp.) and the like, and be restrained within the first configuration within the delivery catheter and self-expandable to the second larger configuration when deployed. In another embodiment, the expandable member can be a self-expandable plug formed of a biocompatible material such as an open or closed cell foam, or a polymer such as polyurethane or silicone.

The extended arm which is directly connected to the expandable member can be integrally formed with the expandable member, or directly connected with a mechanical joint. For example, the mechanical joint may be a weld, solder or melted polyethylene terephthalate (PET). In an embodiment, the integrally formed extended arm and expandable member may be laser cut from the same material. The extended arm can be straight, tapered, and/or bent to meet the requirements of the catheter delivery system in a particular body lumen with regard to flexibility profile and curvature of the body lumen.

The distal ball tip may be formed on a distal end of the extended arm, and may be formed of the same or different material than the extended arm. In an embodiment, the distal end of the extended arm includes a hole, and the distal ball tip of different or same material as the extended arm is formed over the distal end of the extended arm and within the hole.

A tissue ingrowth element, such as a fibers, fibrous mass, porous material, etc. may be provided within, on, or as a part of the expandable member to facilitate tissue growth therein. Tissue growth can be into or onto the expandable member to at least partially occlude the reproductive lumen. Tissue growth may include epithelialization, scar formation, cell proliferation, or other cell growth or multiplication.

These and other features of embodiments of the invention will become more apparent in light of the detailed description of the invention and the exemplary drawings contained herein.

DETAILED DESCRIPTION

Figure 1:
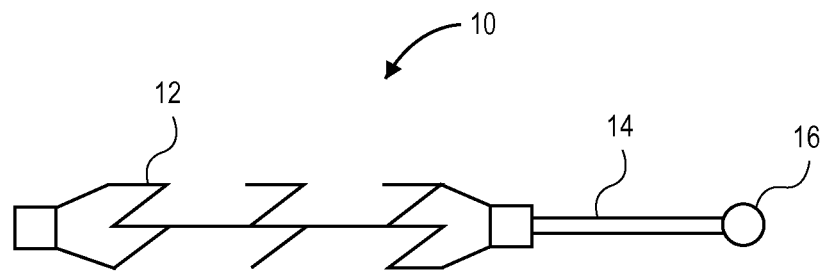
FIG. 1 is a schematic view illustration of an expandable occlusion device in accordance with an embodiment of the invention.

FIG. 1 is a schematic view illustration of an expandable occlusion device 10 in accordance with an embodiment of the invention. As illustrated in FIG. 1, the expandable occlusion device 10 may include an expandable member 12, an extended arm 14 directly connected to the expandable member 12 and extending distally from the expandable member 12, and a distal ball tip 16 on a distal end of the extended arm 14.

Figure 2:
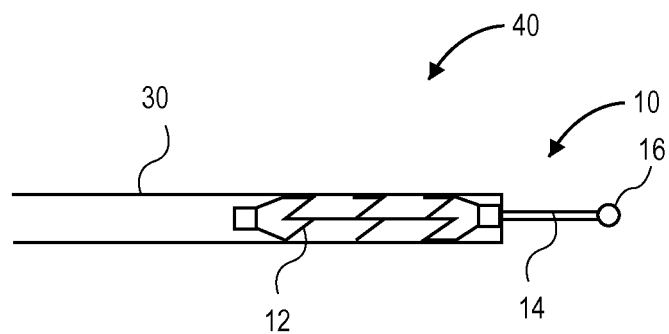
FIG. 2 is a schematic view illustration of a catheter delivery system in accordance with an embodiment of the invention.

FIG. 2 is a schematic view illustration of a catheter delivery system 40 in accordance with an embodiment of the invention. As illustrated in FIG. 2, the expandable occlusion device 10 may be at least partially placed within a delivery catheter 30. In this configuration, the expandable member 12 is placed within the delivery catheter 30, while the distal ball tip 16 and at least a portion of the extended arm 14 remain outside of the delivery catheter 30 such that the extended arm 14 and distal ball tip 16 can function to steer the catheter delivery system 40 when tracking through a body lumen to reach the target delivery site. Once the expandable occlusion device 10 has been tracked to the target location it may be deployed into the body lumen with a variety of techniques such as withdrawing the catheter 30, pushing the expandable occlusion device 10 out of the catheter 30 using a push rod, unscrewing the expandable occlusion device 10, amongst others.

Figure 3:
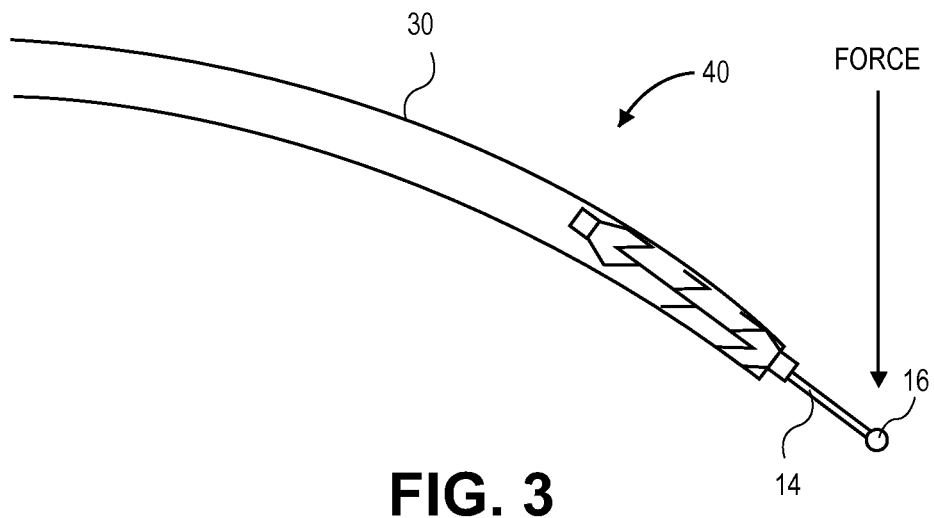
FIG. 3 is a schematic view illustration of a force being applied to a catheter delivery system in accordance with an embodiment of the invention.

In an embodiment, the catheter delivery system 40 is defined by a flexibility profile of a tapered beam. As illustrated in FIG. 3, when a force is applied to the distal end of the catheter system 40, the catheter system may deflect similarly as a tapered beam, e.g. a smooth, gradual increase in flexibility toward the distal end. By way of example, the tapered beam flexibility profile can be more similar to that of a fishing pole that has a tapered cross-section toward the distal end, rather than a pole with a constant cross-section. The gradual transition in flexibility of the catheter delivery system 40 may assist with tracking the catheter through a tortuous body lumen without kinking.

Figure 4:
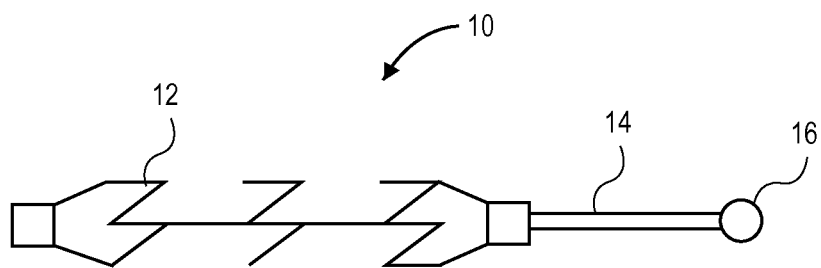
FIG. 4 is a schematic view illustration of an expandable occlusion device including a straight extended arm in accordance with an embodiment of the invention.
Figure 5:
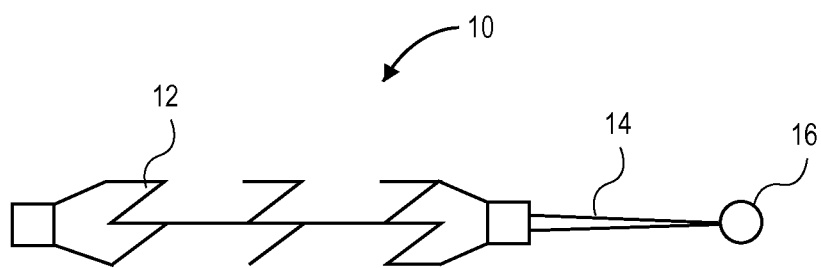
FIG. 5 is a schematic view illustration of an expandable occlusion device including a tapered extended arm in accordance with an embodiment of the invention.
Figure 6:
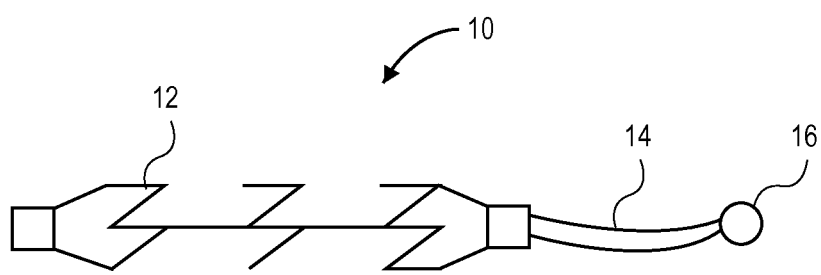
FIG. 6 is a schematic view illustration of an expandable occlusion device including a curved extended arm in accordance with an embodiment of the invention.

The extended arm 14 may take a variety of configurations in accordance with embodiments of the present invention. For example, extended arm 14 may be straight as illustrated in FIG. 4, tapered toward the distal end as illustrated in FIG. 5, or bent as illustrated in FIG. 6. A tapered extended arm 14 may assist in obtaining a smooth, gradual flexibility profile in both the expandable occlusion device 10 and catheter delivery system 40. A bent extended arm 14 may be formed to assist with insertion into a curved body lumen, such that the catheter system 40 can be turned in vivo to match the curvature of the bent extended arm 14 to the curvature of the body lumen when tracking the catheter system 40 though the body lumen. The particular configurations illustrated in FIGS. 4-6 are not meant to be mutually exclusive of one another and may be combined in order to meet the requirements of the catheter delivery system 40 in a particular body lumen with regard to flexibility profile and curvature.

The expandable member 12 may be in a first smaller configuration for delivery in a suitable delivery catheter 30 and expand to a second larger dimensioned second configuration within the body lumen. The expandable member 12 may be formed of a variety of materials in accordance with embodiments of the present invention, such as stainless steel, NiTi alloy (shape memory and superelastic), NiCoCrMo alloy, CoCrNi alloy and the like, as well as other biocompatible materials such as open or closed cell foams, and polymers such as polyurethane and silicone.

Figure 9:
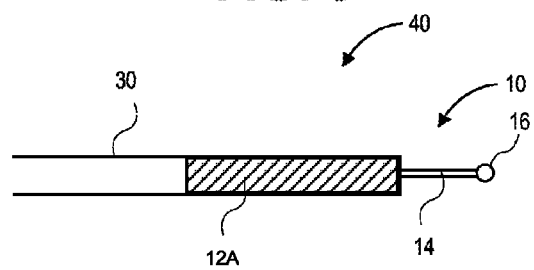
FIG. 9 is a schematic view illustration of a catheter delivery system in accordance with an embodiment of the invention.

In an embodiment, expandable member 12 can be expanded by an inflatable balloon placed within and removable from the expandable member 12. In an embodiment, the expandable member 12 can be self-expandable when not physically restrained, e.g. by the delivery catheter 30. For example, the self-expandable member 12 may be formed of superelastic metal such as a NiTi alloy, which is in a stress induced martensite phase when restrained within the catheter, and which has a stable austenite phase when unrestrained at body temperature. In an embodiment, expandable member 12 is a self-expandable plug 12A, as illustrated in FIG. 9. The plug 12A is configured to be compressible for delivery within a delivery catheter 30 and to be self-expandable within the body lumen when discharged from the delivery catheter 30. The self-expandable plug 12A may be formed of a variety of biocompatible materials such as open or closed cell foams, and polymers such as polyurethane and silicone. In an embodiment, the expandable member 12 may be self-expandable with the application of heat. For example, the self-expandable member 12 may be formed of shape memory metallic material such as NiTi alloy which has a stable martensite phase at body temperature and returns to a remembered expanded configuration when heated to transform the martensite to the austenite phase.

In an embodiment, the expandable member 12 is about 1 to about 5 mm, more specifically about 2 to about 4 mm in transverse dimension in the expanded configuration and about 0.5 to about 8 cm, more specifically about 1.5 to about 4 cm in length. While the description herein is focused on the use of only one expandable member 12, two or more expandable members 12 may be employed in a reproductive lumen.

Figure 7:
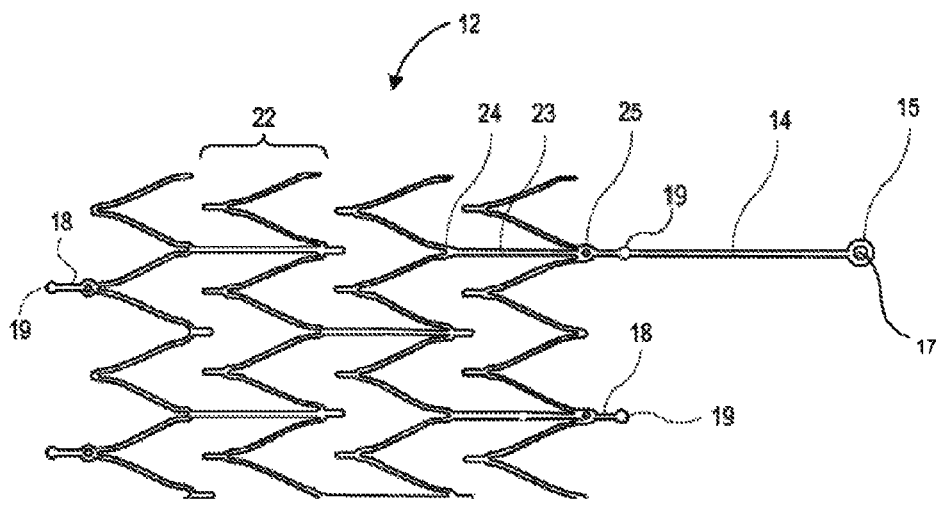
FIG. 7 is a schematic view illustration of a stent-like expandable occlusion frame in accordance with an embodiment of the invention.
Figure 8:
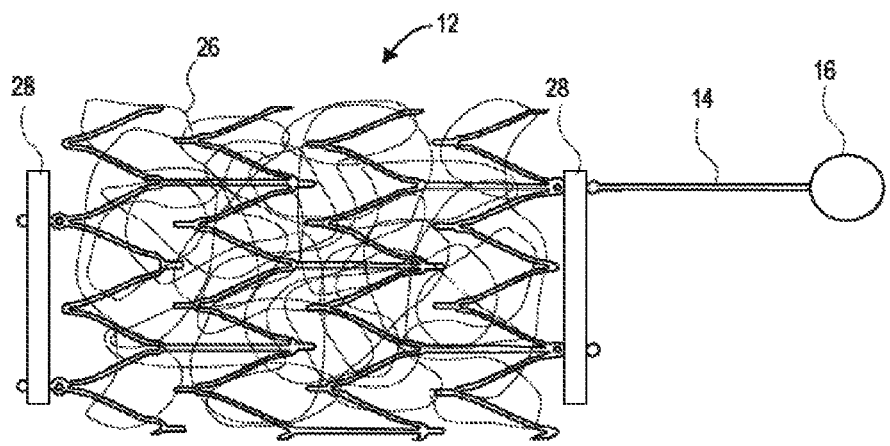
FIG. 8 is a schematic view illustration of a stent-like expandable occlusion device in accordance with an embodiment of the invention.

FIGS. 7-8 are schematic view illustrations of a stent-like expandable frame member 12 in accordance with embodiments of the invention, which may be self-expandable. Referring to FIG. 7, the stent-like expandable frame member 12 may include a plurality of interconnected ring sections 22. The ring sections 22 are interconnected by one or more connecting members 23 extending between the peak 24 of an undulation in one ring section to the valley 25 of an adjacent ring section. The adjacent ring sections are off-set or out of phase so that the peaks of one ring section are aligned with the valleys of an adjacent ring section. In an embodiment, stent-like expandable frame member 12 may include one or more tips 19 at the end of an arm 18 which extends from the proximal or distal ring section 22. The arm 18 may have a length which is less than that of the interconnected ring section 22 or connecting member 23.

An extended arm 14 may extend distally from the stent-like expandable frame member 12 and terminate at a distal end 15. In an embodiment, extended arm 14 may extend from a tip 19. In an embodiment, the distal end 15 may include a hole 17, which may assist in structurally maintaining the distal ball tip 16 illustrated in FIG. 8. In an embodiment, the extended arm 14 has a length that is greater than that of the interconnected ring sections 22 or connecting members 23. In an embodiment, the extended arm 14 has a length between 0.5 and 1.0 cm. The extended arm 14 may be directly connected to the expandable frame member 12 through a mechanical joint or integral formation. For example, the extended arm 14 may be directly connected to the expandable member 12 though a mechanical joint such as a weld, solder, or melted PET fiber (not illustrated). In an embodiment, the extended arm 14 is integrally formed with the expandable frame member 12. For example, a stent-like expandable frame member 12 as illustrated in FIGS. 7-8 may be formed by a laser cutting technique where both the frame 12 and extended arm 14 are cut from the same piece of material. Alternatively, where the expandable member 12 is a plug material, the expandable member 12 and extended arm 14 can be integrally formed from the same mold, for example. In an embodiment, where the expandable member 12 and extended arm 14 are integrally formed (e.g. by laser cutting or molding) the distal ball tip 16 can likewise by integrally formed.

Tissue ingrowth elements such as a fibrous body, porous material etc. may be provided within, on, or as a part of the expandable member 12 to facilitate tissue growth therein and permanent occlusion of the body lumen. FIG. 8 illustrates a fibrous body 26 provided within expandable frame member 12 to facilitate and enhance tissue ingrowth therein. Tissue ingrowth may occur over time around and through the perimeter of the expandable frame member 12 forming a permanent barrier to the passage of biological components. In an embodiment, fibrous body 26 is formed of a material that causes irritation or otherwise stimulates a tissue ingrowth response, e.g. PET, to enhance or accelerate tissue ingrowth. Tissue growth may include epithelialization, scar formation, cell proliferation, or other cell growth or multiplication.

Proximal and distal rings 28 may be provided on the stent-like expandable frame member 12 in order to both keep the proximal and distal ends of the stent-like expandable frame member 12 together and to keep the fibrous body 26 from being dislodged from member 12. As illustrated, the lengths of arms 18 are approximately the same as the width of ring 28, which may be secured to the arms 18 through a variety of means including melted PET, solder or weld.

A distal ball tip 16 may be formed on the distal end 15 of the extended arm 14 by a variety of means including melted PET, solder, and weld. Distal ball tip 16 may be formed of a material different then the extended arm 14. In an embodiment, distal ball tip 16 is formed by heating up a PET fiber and molding/forming it into a ball 16 on the distal end 15. Where the distal end 15 has a hole 17 in it, the material forming the distal ball tip 16 may also flow into the hole 17 thereby further locking the distal ball tip 16 in place. In an embodiment, distal ball tip 16 has a cross-section which is larger than the cross-section of extended arm 14. In an embodiment, distal ball tip 16 has a diameter in a range from about 0.020 inches to about 0.050 inches. While the distal ball tip 16 is characterized as a ball which may have a diameter, it is not necessary to embodiment of the invention that the distal ball tip be spherical or be characterized as having a diameter. The distal ball tip 16 may aid in tracking and navigation through a body lumen while avoiding perforation, and the extended arm 14 may flex laterally to track the tortuous bends often found within a body lumen such as a fallopian tube and to prevent kinking of the catheter system. As previously described, the extended arm 14 in FIGS. 7-8 can be designed to have a specific flexibility profile. The extended arm can assume any of the configurations or combinations thereof as discussed with regard to FIGS. 4-6. While embodiments illustrated in FIGS. 1-8 show a single extended arm 14 and distal ball tip 16, the catheter delivery system and occlusion device may also include a plurality of extended arms 14, at least a portion of which are outside of the delivery catheter 30, with a distal ball tip 16 on a distal end 15 of each of the plurality of extended arms 14. In an embodiment, a plurality of extended arms 14 are directly connected to an expandable member 12, extend distally from the expandable member, and are joined at a single distal ball tip 16.

The expandable occlusion devices 10, catheter systems 40, and methods of using such may be effective over the long term in occluding a body lumen sufficiently to prevent the passage therethrough of undesirable biological elements, e.g. cells. The methods and devices are particularly beneficial for occluding reproductive lumens for contraceptive purposes. Although the occlusion of a patient's reproductive lumens are discussed herein in detail, it can be appreciated that the devices, methods and systems described herein can easily be adapted to occlude a patient's arteries or veins in a variety of situations, the nidus of an arterial-venous malformation, patent ductus arteriosis in infants, as well as arteries feeding blood to cancerous tumors.

Various modifications and improvements may be made to the present invention without departing from the scope thereof. For example, while the invention has been discussed primarily in terms of occluding a reproductive body lumen, the occlusion device may be used to occlude a variety of body lumens or passageways. Moreover, although individual features of the invention may be described with respect to one or more of the embodiments but not in other embodiments, those skilled in the art will recognize that individual features of one embodiment of the invention can be combined with any or all the features of one or more of other embodiments.

What is claimed is:

1. A catheter delivery system comprising:
a delivery catheter;
an occlusion device comprising:
    an expandable member restrained within the delivery catheter; and
    an extended arm directly connected to the expandable member and extending distally therefrom outside of the delivery catheter; and
    a distal ball tip on a distal end of the extended arm, wherein the extended arm is both bent and tapered toward the distal end of the extended arm between a location where the extended arm is directly connected to the expandable member and the distal ball tip;
wherein the distal ball tip and at least a portion of the extended arm remain outside of the delivery catheter such that the extended arm and distal ball tip can function to steer the catheter delivery system when tracking through a body lumen, and the catheter delivery system can be turned in vivo to match a curvature of the bent extended arm to a curvature of a body lumen when tracking the catheter delivery system though the body lumen.

2. The catheter delivery system of claim 1, wherein the extended arm is integrally formed with the expandable member.

3. The catheter delivery system of claim 2, wherein the expandable member is a self-expandable plug.

4. The catheter delivery system of claim 3, wherein the self-expandable plug is formed of a biocompatible material selected from the group consisting of open cell foam, closed cell foam, polyurethane and silicone.

5. The catheter delivery system of claim 2, wherein the tapered cross-section is gradually reduced between the location where the extended arm is directly connected to the expandable member and the distal ball tip.

6. The catheter delivery system of claim 1, wherein the expandable member is a stent-like frame.

7. The catheter delivery system of claim 6, wherein the stent-like frame is self-expandable from a first restrained configuration to a second larger configuration.

8. The catheter delivery system of claim 7, wherein the stent-like frame is formed of a nickel-titanium alloy.

9. The catheter delivery system of claim 8, wherein the nickel-titanium alloy is a superelastic NiTi alloy.

10. The catheter delivery system of claim 1, wherein the extended arm is directly connected to the expandable member with a mechanical joint.

11. The catheter delivery system of claim 10, wherein the mechanical joint is polyethylene terephthalate.

12. The catheter delivery system of claim 1, wherein the distal ball tip is formed from a different material than the extended arm.

13. The catheter delivery system of claim 1, further comprising:
    a second extended arm directly connected to the expandable member and extending therefrom; and
    a second distal ball tip on a second distal end of the second extended arm.

14. The catheter delivery system of claim 1, wherein the occlusion device and the delivery catheter form the catheter delivery system defined by a tapered beam flexibility profile.

* * * * *